United States Patent
Ljungberg

(10) Patent No.: US 12,029,531 B2
(45) Date of Patent: Jul. 9, 2024

(54) SYSTEM FOR COLLECTING LUNG FUNCTION DATA

(71) Applicant: MEDITUNER AB, Stockholm (SE)

(72) Inventor: Henrik Ljungberg, Stockholm (SE)

(73) Assignee: MEDITUNER AB, Stockholm (SE)

( * ) Notice: Subject to any disclaimer, the term of this patent is extended or adjusted under 35 U.S.C. 154(b) by 0 days.

(21) Appl. No.: 18/270,425

(22) PCT Filed: Dec. 31, 2021

(86) PCT No.: PCT/EP2021/087897
§ 371 (c)(1),
(2) Date: Jun. 29, 2023

(87) PCT Pub. No.: WO2022/144443
PCT Pub. Date: Jul. 7, 2022

(65) Prior Publication Data
US 2023/0389807 A1    Dec. 7, 2023

(30) Foreign Application Priority Data

Dec. 31, 2020    (GB) ..................................... 2020820

(51) Int. Cl.
*A61B 5/0205*    (2006.01)
*A61B 5/00*    (2006.01)
(Continued)

(52) U.S. Cl.
CPC .......... *A61B 5/0205* (2013.01); *A61B 5/1112* (2013.01); *A61M 15/0001* (2014.02);
(Continued)

(58) Field of Classification Search
None
See application file for complete search history.

(56) References Cited

U.S. PATENT DOCUMENTS

2010/0089394 A1   4/2010   Sakurada et al.
2013/0317379 A1   11/2013  Brimer et al.
(Continued)

FOREIGN PATENT DOCUMENTS

WO    2020047102 A1    3/2020

OTHER PUBLICATIONS

International Search Report and Written Opinion for Application No. PCT/EP2021/087897, dated Mar. 10, 2022.
(Continued)

*Primary Examiner* — Jay B Shah
(74) *Attorney, Agent, or Firm* — Kevin E. West; Advent, LLP

(57) ABSTRACT

According to at least one embodiment, a system for collecting lung function data is provided. The system may comprise a, preferably mobile and hand-held, spirometer (20) for measuring lung function and providing lung function data (24); and a mobile hand-held computer (30), for example a mobile phone, comprising a processor (35), a memory (36), a clock (37), and a screen (38), and preferably a GPS. The spirometer (20) and the mobile hand-held computer (30) are separate devices, and the spirometer (20) and the mobile hand-held computer (30) communicate electronically. The processor (35) is configured for collecting the measured lung function data (24) from the spirometer (20) via the electronic communication between the spirometer (20) and the mobile hand-held computer (30), and storing the lung function data (24) in the memory (36). The processor (35) is further configured for collecting, starting to collect, with the system lung function data (24), the measurements, from the spirometer (20) by indicating electronically on, for example on the screen (38) of, and/or through sound indications from, the mobile hand-held computer (20) to use the spirometer (20).
(Continued)

The system indicates to start collecting lung function data only when A) and/or B), and in addition, as described further below, only when C) and/or D). The system is thus configured to indicate when to use the spirometer to take a measurement so that relevant lung function data can be collected, in an efficient manner, and in the shortest time possible. A) Is when the clock (37) reaches a predetermined time regularly within 24 hours, preferably twice a day. This may be set by the user of the system using the mobile hand-held computer. It may be regularly, recurring at intervals, within 24 hours. For example, a very effective collection is done when it is twice a day, during day time, with at least 10 hours between, such as one in the morning and once in the evening. B) Is before and after the mobile hand-held computer (30) indicates to take any medication, such as lung medication, or after the mobile hand-held computer (30) indicates that any medication has been taken. After taking a measurement, the processor (35) is further configured to calculate, by the processor (35), a variation between all collected lung function data (24) stored in the memory (36). After having calculated the variation, the processor (35) is configured to stop the system to collect measurements from the spirometer (20), or indicate on the screen (38) to stop using the spirometer (20), when the processor (35) compares the variation between all collected lung function data (24) is more than 20 percent, or after a maximum of collecting lung function data for 14 days. This ensures that relevant measurements, quality measurements, and enough measurements have been collected.

7 Claims, 1 Drawing Sheet

(51) Int. Cl.
 *A61B 5/024* (2006.01)
 *A61B 5/087* (2006.01)
 *A61B 5/11* (2006.01)
 *A61M 15/00* (2006.01)

(52) U.S. Cl.
 CPC ............... *A61B 5/024* (2013.01); *A61B 5/087* (2013.01); *A61B 5/742* (2013.01)

(56) References Cited

U.S. PATENT DOCUMENTS

| | | |
|---|---|---|
| 2014/0316296 A1 | 10/2014 | Meng et al. |
| 2017/0007159 A1 | 1/2017 | Dieffenderfer et al. |
| 2019/0192046 A1 | 6/2019 | Ljungberg |
| 2020/0001026 A1 | 1/2020 | Starr et al. |

OTHER PUBLICATIONS

Written Opinion of the International Preliminary Examining Authority for Application No. PCT/EP2021/087897, dated Jul. 8, 2022.

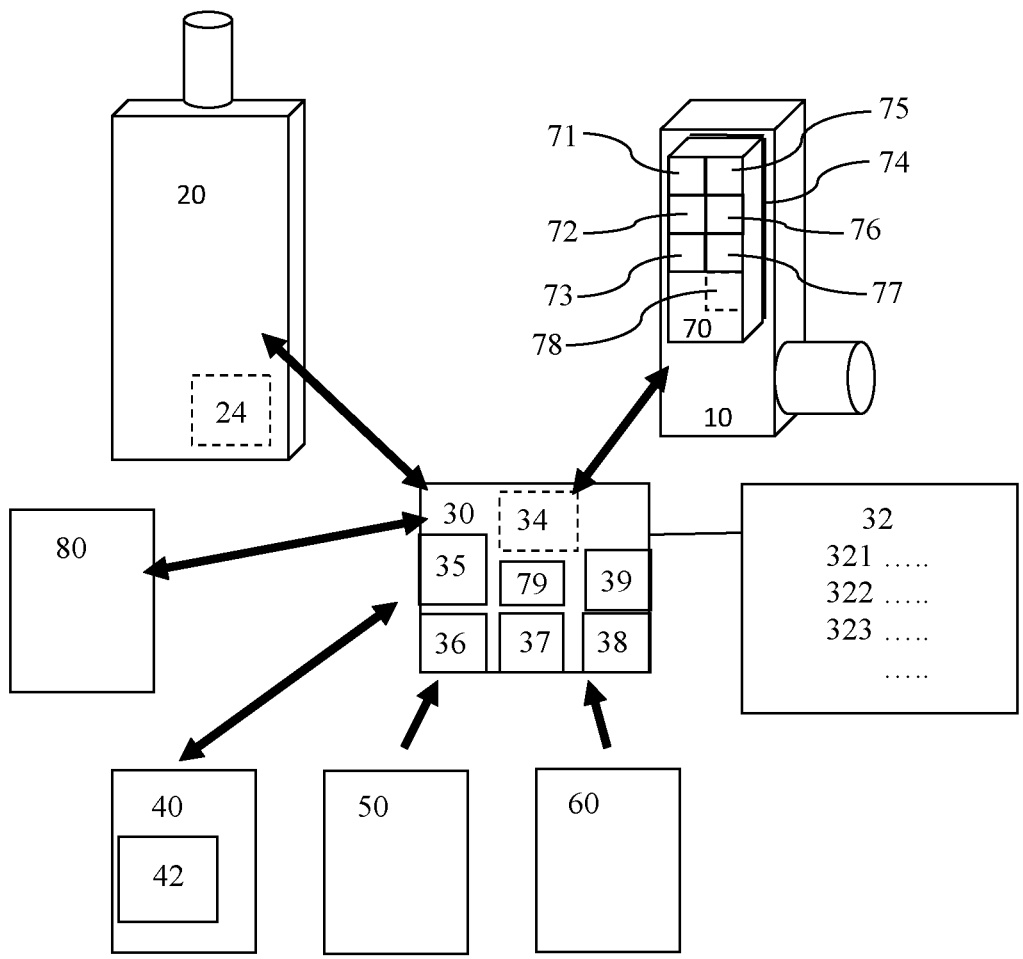

SYSTEM FOR COLLECTING LUNG FUNCTION DATA

TECHNICAL FIELD

The present disclosure relates to collecting lung function data. More particularly, the present disclosure relates to a system for collecting lung function data with a spirometer and sensor for a mobile hand-held inhaler.

BACKGROUND

In recent years attention has been turned to lung function. Measuring different data of the human body, such as height, weight, and lung volume is always desirable. Lung function data are for example used for the purpose of giving a picture of the lungs. However, it is a problem to collect relevant lung function data, in an efficient manner, and in the shortest time possible, and when to start collecting and when to stop collecting, so that relevant lung function data is collected. It is further a problem how to improve quality of lung function data. A single measurement of lung volume does not give relevant lung function data. Several hundreds of measurements of lung volume may give relevant lung function data, but takes normally more than two months to collect, and there is no guarantee of the quality of such data. WO 2020/047102, US 2014/316296, US 2010/089394, and US 2013/317379 may be useful for understanding the background.

It is further a problem when collecting lung function data that various factors influence the data collected and distorts the data. What factors influences and how is a problem. It is a problem how to collect lung function data using technology, in an automatic manner, and in situ. For example, a visit to a laboratory each time data must be collected is not an option. It is also a problem how to make a spirometer measurement correct and proper. How to make spirometer measurement without the supervision of a nurse or a doctor during the measurement is a problem. It is a problem how to save energy for the equipment that is used for collecting lung function data.

A technical restriction is the existing products on the marked, such as mobile hand held computers, mobile phones, spirometers, and inhalers and the desire to provide a system that is compatible with products. Furthermore, the systems in place and national law and restriction concerning medical systems put a limitation on what can be done. To improve evidence-based care, it is desirable, also by a national board of health and welfare to address problems such as: close follow-up and regular symptom monitoring; regular measurements of lung function; increased education of health care staff and patients; and individualized treatment plans for all patients. It is a problem how to automate this so that more patients can have their individual treatment plans according to recommendations and, in addition, how it can be provided so that they have it with them wherever they may need it. The recommended regular measurement of lung function is time consuming and expensive as it has to be performed several times before and after medication at a clinic by a trained nurse, and afterwards the result has to be interpreted by a physician.

It is a problem how to provide a computer controlled dosage system where the system has as full as possible control of the dosage. The dosage instructed may vary from the dosage taken. It is further a problem to provide an adaptor that fits all inhalers, because inhalers are different in shape and function. It is a problem to know whether a dose has been administered from the inhaler and furthermore if the inhaler has been used in the correct manner. How to provide an adaptor that can give information about an inhaler is a problem, because inhalers are different in shape and function.

SUMMARY

It is an object of the present invention to provide a system for collecting lung function data. This object can be achieved by the features as defined by the independent claims. Further enhancements are characterized by the dependent claims.

Embodiments disclosed herein provides a computer controlled dosage system having as full as possible control of the dosage. This may be done by providing a computer controlled dosage system that measures, senses, the dosage/medication given and the effect the dosage/medication has made, in conjunction with a treatment plan, especially a treatment plan that is adapted and personalized by the system.

Embodiment disclosed herein provides an adaptor, a sensor, that fits all inhalers, even if the inhalers are different in shape and function. This may be done by measuring sound, vibrations, that is caused by the inhaler when delivering medication.

According to one embodiment, a system for collecting lung function data may collect relevant lung function data, in an efficient manner, and in the shortest time possible. The system may improve quality of lung function data. The system allows for handling various factors influencing the data collected without distorting the data. The system collects lung function data using technology, in an automatic manner, and in situ. At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed and/or described embodiment herein may be technically combined with any other claimed and/or described embodiment(s).

BRIEF DESCRIPTION OF THE DRAWINGS

The accompanying drawings illustrate presently preferred exemplary embodiments of the disclosure, and together with the general description given above and the detailed description of the preferred embodiments given below, serve to explain, by way of example, the principles of the disclosure.

FIG. 1 is a diagrammatic illustration of some exemplary embodiments of the present disclosure.

DETAILED DESCRIPTION

FIG. 1 illustrated a system for collecting lung function data. This system collects data represented as electronic data of the lungs of a user of the system. The measured lung function may for example be lung volume, inhaled or exhaled air volume or air flow, peak expiratory flow, or forced expiratory volume, or any combination thereof. The schematic illustration on FIG. 1 applies to all different embodiments disclosed herein. While embodiments have partly been disclosed separately, any embodiment can be combined with any other embodiment, or embodiments, described herein, in the FIGURE and in the claims.

Collecting Data

According to at least one embodiment, a system for collecting lung function data is provided. The system may comprise a preferably mobile and hand-held, spirometer (20) for measuring lung function and providing lung function data (24); and a mobile hand-held computer (30), for example a mobile phone, comprising a processor (35), a memory (36), a clock (37), and a screen (38), and preferably a GPS (39). The spirometer (20) and the mobile hand-held computer (30) are separate devices, and the spirometer (20) and the mobile hand-held computer (30) are configured to communicate electronically with each other. The communication may be wireless data communication.

The processor (35) is configured for collecting the measured lung function data (24) from the spirometer (20) via the electronic communication between the spirometer (20) and the mobile hand-held computer (30), and storing the lung function data (24) in the memory (36). The processor (35) is thus configured to get the measured lung function data (24), such as for example lung volume, from the spirometer (20) after a user has used the spirometer (20). The data collected from the spirometer (20), sent from the spirometer (20) to the mobile hand-held computer (30), is then stored in the memory (36).

The processor (35) is further configured for collecting, starting to collect, with the system lung function data (24), the measurements, from the spirometer (20) by indicating electronically on, for example on the screen (38) of, and/or through sound indications from, the mobile hand-held computer (20) to use the spirometer (20). The system indicates to start collecting lung function data only when A) or B), and in addition, as described further below, only when C) and/or D). That is, the processor (35) is configured for both A) and B) and when one of the conditions A) or B) occurs, then, and only then, the mobile hand-held computer (20) indicates to use the spirometer (20). As described further below, the processor (35) may also indicate to use the spirometer (20) when the condition C) and/or D) occurs. The processor (35) may be configured for A) and B) and C) and when one of the conditions A) or B) or C) occurs, then, and only then, the mobile hand-held computer (20) indicates to use the spirometer (20). The processor (35) may be configured for A) and B) and C) and D) and when one of the conditions A) or B) or C) or D) occurs, then, and only then, the mobile hand-held computer (20) indicates to use the spirometer (20). The processor (35) may be configured for A) and B) and D) and when one of the conditions A) or B) or D) occurs, then, and only then, the mobile hand-held computer (20) indicates to use the spirometer (20). The system is thus configured to indicate when to use the spirometer to take a measurement so that relevant lung function data can be collected, in an efficient and energy saving manner, and in the shortest time possible.

A) Is when the clock (37) reaches a predetermined recurring time within 24 hours. For example A) is when the clock (37) reaches a predetermined time regularly within 24 hours, preferably twice a day. This may be set by the user of the system using the mobile hand-held computer. It may be regularly, recurring at intervals, within 24 hours. For example, a very effective and energy saving collection is done when it is twice a day, during day time, with at least 10 hours between, such as for example once in the morning and once in the evening.

B) Is before and after the mobile hand-held computer (30) indicates to take any medication, such as lung medication, or after the mobile hand-held computer (30) indicates that any medication has been taken. The processor (35) may be configured to make an indication, for example via the screen (38), to a user to take a medication. The processor (35) may be configured to indicate to use the spirometer (20) before and after such an indication. The processor (35) may be configured to indicate to use the spirometer (20) after such an indication. After taking a measurement, the processor (35) is further configured to calculate, by the processor (35), a variation between all collected lung function data (24) stored in the memory (36). This calculation is done each time lung function data is collected from the spirometer (20). The variation may be calculated as ((highest lung function data−lowest lung function data)×100/(highest lung function data+lowest lung function data)×0.5). The lung function data may be the lung volume. The variation is the coefficient of variation expressed in percentage.

The processor (35) is configured for repeating the indication to use the spirometer only when A) or B) and repeating the calculation of the variation, until the variation between all collected lung function data (24) is more than 20 percent, or after a maximum of collecting lung function data for 14 days. The same spirometer (20) is used during this. After having calculated the variation, the processor (35) is configured to stop the system to collect measurements from the spirometer (20), or indicate on the screen (38) to stop using the spirometer (20), when the processor (35) compares the variation between all collected lung function data (24) is more than 20 percent, or after a maximum of collecting lung function data for 14 days. This ensures that relevant measurements, quality measurements, and enough measurements have been collected. This also ensures that the whole system saves energy because the system needs not to collect more measurements. This solves several technical problems related to how to collect relevant data while saving energy. This is achieved by configuring the system to start collecting and continue to collect data only when A) or B) and to stop when the variation is over 20 percent. Prior art systems use several months to collect data, and the data is normally not collected in an efficient manner and this results in a lot of energy loss and time loss.

The maximum may be set to 21 days. According to other embodiment, the system is configured to stop collecting data when the variation is equal to, or larger than, fifteen percent, preferably 20 percent, 25, or 30 percent.

The spirometer (20), or other devices, and the mobile hand-held computer (30) communicate electronically with each other. This means sending and receiving data between each other by cable or preferably via wireless, e.g. Bluetooth. For example, the mobile hand-held computer sends data to a monitor (80) asking for heart rate data, and the monitor (80) sends heart rate data from the monitor to the handheld mobile device.

According to one embodiment, a heart rate monitor (80) may be added to the system described above. The system may further comprise a measuring device (80) for measuring the heart rate, for example pulse of a user of the system, and providing heart rate data of the user, the user of the spirometer (20). The measuring device (80) may be a separate device from the spirometer (20) and the mobile hand-held computer (30), and the measuring device and the mobile hand-held computer may communicate electronically, sending measured data and commands to each other. The processor (35) may be further configured for collecting the measured heart rate data from the measuring device (80) via the electronic communication between the measuring device (80) and the mobile hand-held computer (30), and storing the heart rate data in the memory (36). When to collect data, when starting to collect data, i.e. the measurements from the spirometer may be done in the following way. Indicating on, for example the screen of, the mobile hand-held computer when to use the spirometer only when A) or B) or C). The indication may be done by sound from the mobile hand-held computer (30).

C) Is when the measuring device measures a heart rate of 85 percent, or more, of a max value of the heart rate. The max value may be the historic max, i.e. the highest heart rate of a user of the system, and/or the max value may be calculated according to normative values of the heart rate collected during the measurements. The max value may be the highest heart rate measured since the system has indicated to use the spirometer (20) for the first time during collecting lung function data. Once the system stops collecting lung function data, then the max value may be reset. Any data, e.g. time such as when and how long, related to the heart rate may also be collected in the memory (36).

By starting to collect measurements from the spirometer (20), and then collecting a measurement when A) or B) or C) occurs, and then stopping as described above, ensures that that relevant measurements, quality measurements, and enough measurements have been collected, and collected in an energy efficient way. The above described embodiments may be combined with any of the embodiments described below.

According to one embodiment, the heart rate measurement in C) has a time period, a duration, of at least 5 to 10 minutes, preferably 8 minutes. The processor (35) may be further configured to subsequently indicate, for example on the screen or by sound, on the mobile hand-held computer (30) to use the spirometer 5 minutes after the time period has ended. Alternatively, it may be 10, 15, or 30 minutes after the time period has ended. However, the duration of 5 to 10 minutes, preferred 8 minutes, achieves the technical effect of saving energy while collecting efficiently relevant lung function data.

Sensor

According to one embodiment, any one of the embodiments described above or below, the system may further comprise a hand-held inhaler (10) for providing lung medication; and a sensor (70) measuring sound and/or vibration. The sensor (70) may be attached to the hand-held inhaler (10) and the sensor (70) may be measuring sound made by the inhaler. The sensor (70) may be a part separate from the hand-held inhaler (10), but attachable to the inhaler (10). The sound may be generated for example by operating the inhaler, such as, for example, a "click" or release of aerosol, and/or the sound generated by air flow through the inhaler when inhaling. In addition, or separately, the sensor may be measuring vibrations caused by operating the hand-held inhaler (10) to provide medication, for example lung medication. Some inhalers need to be shaken before the dose is administered. The sensor may contain an accelerometer that ensures that correct shaking has occurred. The sensor (70) and the mobile hand-held computer (30) may be configured to communicate electronically with each other, e.g. sending data and commands wireless to each other. The processor (35) may further be configured for analyzing the measured sound and/or vibrations to determine if the hand-held inhaler (10) has provided medication, for example lung medication, and then indicate that medication has been taken in B) and to use the spirometer (20). This may be done, for example, by the processor (35) being configured to measure the inhalation sound and duration of inhalation through the inhaler. The sensor (70) may be a sensor adapter as described below.

According to one embodiment, the system may further comprise a hand-held inhaler (10) for providing lung medication; and a sensor (79) measuring sound and/or vibration, the sensor (79) being integrated in the mobile hand-held computer (30) and the sensor (79) measuring sound and/or vibrations caused by operating the hand-held inhaler (10) to provide lung medication. This embodiment does not require a sound and/or vibration sensor (70) on the inhaler (10). For example, when the mobile hand-held computer (30) is within a 50 cm distance from the hand-held inhaler (10) then the mobile hand-held computer (30) may sense the sound or vibration. The sensor (79) within the mobile hand-held computer (30) communicates electronically with the mobile hand-held computer (30). Some inhalers need to be shaken before the dose is administered. The mobile hand-held computer (30) may contain an accelerometer that could be held in the same hand as the inhaler to ensure that correct shaking has occurred. The processor (35) may be further configured for analyzing the measured sound and/or vibrations to determine if the hand-held inhaler (10) has provided lung medication and then indicate that lung medication has been taken in B) and to use the spirometer (20) to make a measurement. The sensor (79) may be configured and work correspondingly as the sensor adapter described below. According to one embodiment, to be combined with any other embodiment disclosed herein, the processor (35) may be further configured for analyzing the measured sound and/or vibrations to determine if a user has laughed or coughed. In such a case the processor (35) may indicate to the user that the spirometer (20) should be used. The processor (35) may then also be configured to cause the hand-held mobile computer (30) to give an alarm so to wake up the user if the user is asleep. In this way the system collects efficiently all relevant lung function data. Any data, e.g. such a time, related to the use of the spirometer, laughter, or cough, may also be collected in the memory (36).

GPS

According to one embodiment, the system may further comprise a GPS (Global Positioning System, 39). The processor (35) may be further configured for retrieving the location of the mobile hand-held computer. The collection of, or starting to collect, measurements from the spirometer (20) by indicating electronically on the screen of, and/or by sound from, the mobile hand-held computer (30) to use the spirometer (20) only when A) or B) or C) or D), or only when A) or B) or D). Where D) is when the processor (35) is further configured for analyzing, by using the GPS (39), if the mobile hand-held computer (30) is located within a predetermined area. Such an area can be based on a certain height, the radius from a center of a city, a pollen area, or a predetermined distance moved by the GPS (39) during a time period. For example, an athlete who does a specific amount of running, or walking, in kilometers per time. Hereby it is ensured that relevant measurements, quality measurements, and enough measurements have been collected depending on such a running or walking activity. The collection of lung function data with the spirometer may be done when criteria D) occurs, which is when the processor (35) is further configured for analyzing, by using the GPS (39), if the mobile hand-held computer (30) has moved a predetermined distance during a predetermined time period, for example if the mobile hand-held computer (30) moves with a certain predetermined speed for a certain predetermined duration. Any data related to the predetermined area, speed and duration may also be collected in the memory (36).

The system described above, and below, solves the problem of saving energy while at the same time collect relevant lung function data efficiently. The efficiency includes not collecting a lot of lung function data that is not relevant, thus concentrating on relevant lung function data, and not collecting a lot of data for a long time, e.g. more than several weeks, normally months. The configuration of the mobile hand-held computer (30) and its processor (35), the spirometer (20) and the other features allows the claimed system to save energy, use less energy, save battery, use less processing energy and power. The lung function data is also because of the configuration of the features collecting the data faster during a shorter period of time than the prior art, the collection is more efficient. These technical effects are achieved by the system being configured for both A) and B) and when one of the conditions A) or B) occurs, then, and only then, the mobile hand-held computer (20) indicates to use the spirometer (20). The processor (35) may also indicate to use the spirometer (20) when the condition C) and/or D) occurs. The processor (35) may be configured for A) and B) and C) and when one of the conditions A) or B) or C) occurs, then, and only then, the mobile hand-held computer (20) indicates to use the spirometer (20). The processor (35) may be configured for A) and B) and C) and D) and when one of the conditions A) or B) or C) or D) occurs, then, and only then, the mobile hand-held computer (20) indicates to use the spirometer (20). The processor (35) may be configured for A) and B) and D) and when one of the conditions A) or B) or D) occurs, then, and only then, the mobile hand-held computer (20) indicates to use the spirometer (20). An additional feature that brings about the technical effects is when to stop the collection of data. This is done when the processor (35) compares the variation between all collected lung function data (24) and it is more than 20 percent, or after a maximum of collecting lung function data for 14 days, no longer. It is these configurations that allows the system to collect relevant lung function data efficiently and quickly, using a low amount of energy. These technical effects are important to the claimed system, because the system can be carried around with the user and has therefore not an endless amount of energy, nor does the user want to carry the system for a long time.

It is a problem that patients do not take inhaled medications as prescribed. The result is poor health or worsened medical condition. There are some solutions for this problem that exist, usually by detecting activation of a device by a pressure sensitive attached (or built in) button. Some devices use a built in flow sensor that measures inhalation through the device. These sensors are specific to a certain brand or design of inhaler. None of those solutions can give full information on if the medication has been administered correctly. The solutions that disclosed herein are unique in that they may be used with any inhaler regardless of design or brand and can detect 1) shaking of the inhaler if required for that specific device, 2) activation of the inhaler through detecting sound and/or vibration, and 3) inhalation sound and duration of inhalation through the inhaler. To any skilled person the advantages of this device is clearly evident.

Sensor Adapter to an Inhaler

According to one embodiment, an adapter for a mobile hand-held inhaler is provided. This embodiment may be combined with any of the embodiments described herein. The adapter (70) comprises a battery (71), a memory (72), a processor (77), and a sensor (73) measuring sound and/or vibration. Some inhalers need to be shaken before the dose is administered. The sensor may contain an accelerometer that ensures that correct shaking has occurred. The adapter (70) may also comprise a fastener (74) for attaching the adapter to the mobile hand-held inhaler, and a transmitter (75) and a receiver (76) for communicating electronically with an external mobile hand-held computer (30). The data communication also apply to data from the accelerometer. The processor (77), and/or the adapter (70), is configured for using the sensor (73) to sense/measure sound and/or vibrations caused by operating the mobile hand-held inhaler (10) to provide lung medication, for storing the sensed sound and/or vibrations as data (78) in the memory (72), and for communicating the stored data (78) to the external mobile hand-held computer (30). The adapter may be a separate from the mobile hand-held inhaler (10) and may be attachable to the mobile hand-held inhaler (10). It may be removable attached so that it can be removed when the inhaler is empty and is changed. The adapter is comparably small when compared to the inhaler. The adapter may be only 2-5 square centimeters, and less than half a centimeter in thickness, in size. One preferred shape and size is round and 1 cm in diameter. This shape and size would be attachable, e.g. like a sticker, to an outside surface of an inhaler (10). This has as a technical effect that the adapter, with or without an accelerometer, may be attachable to an outside housing of substantially all inhalers (10) on the market. This makes the adapter (79) very adaptable to any mobile hand-held inhaler (10).

According to one embodiment, the processor (77), and/or the adaptor (70), is further configured for storing the sensed sound and/or vibration data; and further configured for communicating the stored data to the external mobile hand-held computer (30) when the transmitter and receiver can communicate electronically, for example are in range, with the external mobile hand-held computer (30).

According to one embodiment, the fastening means is adhesive or elastic means. The elastic means may surround, for example a part of, the inhaler.

According to one embodiment, a computer controlled dosage system, for dosage adjustment for a mobile, hand held, inhaler (10) for delivering a dosage of a medicine, is disclosed. The computer controlled dosage system may comprise a spirometer (20) for measuring lung function (24); an adaptor (70) for sensing sound and/or vibration, as disclosed herein, the adaptor being attachable to the mobile, hand-held, inhaler (10); and a handheld mobile computer (30) separate from the inhaler (10), separate from the spirometer (20), and separate from the adaptor (70), the computer (30) being configured to communicate electronically with the spirometer (20) and the adaptor (70). The computer (30) may comprise a processor (35), a screen (38), a memory (36), and a GPS (39). The processor (35) of the computer (30) may be configured to receive a manual input (50) for storage in the memory (36) of the computer (30). The processor (35) of the computer (30) may be configured to receive measured lung function data electronically, e.g. wireless data communication, from the spirometer (20), and to store lung function data in the memory (36) of the computer (30). The processor (35) of the computer (30) may be configured to create a data set (32) for setting a plurality of levels of different dosages (321, 322, 323) of medicine based on at least the medicine used by the inhaler (10), and the manual input (50). The processor (35) of the computer (30) may be further configured to store the data set (32) in the memory (36) of the computer (30). The data set (32) may be stored only in memory (36), not on a remote server or web server, so that the data set (32) is readily available to the system at any time. The processor (35) being further configured for analyzing the measured sound and/or vibrations to generate an indicator, for example an adaptor use indicator, if the hand-held inhaler has provided lung medication, and then preferably indicate to the computer (30) that lung medication has been taken. The processor (35) may be further configured to generate an indication (34) on the screen (38), or a sound, indicating a dosage adjustment for the inhaler (10), based on at least the measured lung function (24), the use indicator, and on one of the plurality of levels of dosage (321, 322, 323) of the data set, the indication (34) indicating one of the plurality of levels of dosage (321, 322, 323) of the data set (32) as the dosage adjustment for the inhaler (10).

According to one embodiment, the processor (35) is further configured to improve analyzing the sound and/or vibration data by, in response to the indication (34) to use inhaler dosage adjustment, store the sound and/or vibration occurring during providing the medication of the inhaler; and use the known sound and/or vibration to further improve future analyzation of the sound and/or vibration to generate the use indicator.

According to one embodiment, the processor (35) is further configured for improving analyzing the sound and/or vibration data by, receiving the manual input (50) indicating that a user of the system is going to use the inhaler; store the sound and/or vibration occurring during the use of the inhaler providing the medication; and use the known sound and/or vibration to further improve future analyzation of the sound and/or vibration to generate the use indicator. The processor (35) may store characteristics, e.g. frequency, amplitude, pitch, wavelength, normal sound but also above 20 kHz (ultrasound) and below 20 Hz (infrasound), of the sound and vibration of a specific inhaler for the purpose of comparing and recognizing later use of the same specific inhaler. The processor (35) may also store which specific inhaler the stored characteristics relate to. The characteristics of the sound and vibration of a specific inhaler may be updated and taken as an average for the same characteristics during a plurality of usages of the inhaler to improve the analyze of the sound and/or vibration data.

According to one embodiment, the adapter (70) stores the measured sound and/or vibration until the handheld mobile computer (30) communicates electronically with the transmitter and receiver of the adaptor (70) to download the stored sound and/or vibration data to the memory (36) of the handheld mobile computer. The adapter (79) may be configured to store the measurements in the memory (72) and later, when wirelessly connected to the mobile hand-held computer (30), transfer the measurement data so that the processor (35) can store them in the memory (36).

According to one embodiment, the spirometer and/or the sensor measures acceleration and duration of flow and volume to determine a user's capacity to use a specific inhaler. This allows the system to determine a suitable inhaler for a user. The system may include that the processor (35) is configured to indicate, e.g. via the screen (38), what kind of inhaler is the most suitable inhaler for a user, for example indicate that a gas driven inhaler or a non gas driven inhaler is the most suitable.

According to one embodiment, a computer controlled dosage system, for dosage adjustment for a mobile, hand held, inhaler (10) for delivering a dosage of a medicine, is disclosed. Here the sensor (79) may be in the handheld mobile computer (30). The computer controlled dosage system may comprise a spirometer (20) for measuring lung function (24); a handheld mobile computer (30) separate from the inhaler (10), separate from the spirometer (20), and comprising the adaptor/sensor (70), the computer (30) being configured to communicate electronically with the spirometer (20) and the adaptor/sensor (79), the computer (30) comprising a processor (35), a screen (38), the sensor (34) for measuring sound, of the inhaler providing medication, and a memory (36). The processor (35) of the computer (30) may be configured to receive a manual input (50) for storage in the memory (36) of the computer (30). The processor (35) of the computer (30) may be configured to receive measured lung function data electronically from the spirometer (20), and to store lung function data in the memory (36) of the computer (30). The processor (35) of the computer (30) may be configured to create a data set (32) for setting a plurality of levels of different dosages (321, 322, 323) of medicine based on at least the medicine used by the inhaler (10), and the manual input (50). The processor (35) of the computer (30) may be further configured to store the data set (32) in the memory (36) of the computer (30). The processor (35) may be further configured for analyzing the measured sound to generate a use indicator, indicating if the hand-held inhaler has provided lung medication, and then preferably indicate that lung medication has been taken. The processor (35) may be further configured to generate an indication (34) on the screen (38), or as a sound, indicating a dosage adjustment for the inhaler (10), based on the measured lung function (24), the use indicator, and on one of the plurality of levels of dosage (321, 322, 323) of the data set, the indication (34) indicating one of the plurality of levels of dosage (321, 322, 323) of the data set (32) as the dosage adjustment for the inhaler (10). In this embodiment, where the sensor (79) is within the handheld mobile computer (30), the processor (35) is further configured for improving analyzing the sound and/or vibration data as described above for the embodiments where the sensor (70) is on the inhaler (10), which apply correspondingly. The embodiment described above where the sensor (70) is on the inhaler (10) and where the spirometer and/or the sensor measures acceleration and duration of flow and volume to determine a users capacity to use a specific inhaler, also apply correspondingly to this embodiment where the sensor (79) is within the handheld mobile computer (30).

Improved Spirometer Measurement

According to one embodiment, that may be combined with any other embodiment disclosed herein, a system to improve how to make a spirometer measurement is disclosed. It is desirable to have a system that can make a spirometer measurement in a correct way, without the supervision of medical staff. A system that instruct and/or correct a user to make a correct spirometer measurement is preferred. By considering the flow curve representing flow per volume on the y-axis and time on the x-axis an assessment may be made if a correct spirometer measurement has been made. The processor (35) in the embodiments disclosed herein may be configured to assess the flow curve, the spirometer measurements over time, made by one exhale or inhale of a user. If the curve is acceptable, for example smooth enough, no sharp or sudden changes, then the spirometer measurement is accepted. However, if the flow curve have sudden changes, or does not start or end in the normal acceptable way, then the system may give one or more indicators, feedback, to the user to change how the spirometer measurement is done, how the inhale or exhale is done. For example the system may indicate "OK" if the inhale or exhale is correct, "blow longer" or "inhale longer" or "exhale longer" if the flow curve is too short, "blow harder" or "inhale harder" if the flow curve is not high enough, "continue", etc. In this way the feedback may improve and result in a proper and acceptable spirometer measurement.

According to one embodiment, such a system may comprise a patient smartphone application, a portable wireless spirometer (20) for measuring serial lung function of PEF/forced expiratory volume in one second (FEV1), and a healthcare interface including a treatment plan. Such an electronically support systems may provide daily percentage calculations of diurnal or regular variability of PEF/forced expiratory volume in one second (FEV1). With training and the feedback, it is possible to perform the spirometry without the patient having to go to a clinic. This allows a user to perform spirometry according to national, or state, regulations and recommended guidelines. Normally a user need assistance or very clear instructions to perform spirometry that is usually provided by a nurse in the clinic. The computer based system overcomes this by giving feedback in real time and allow a user to perform spirometry correctly anywhere. Assessment of the result can be made by a computer based system. By collecting large volumes of data, the ability to perform spirometry correctly by a user on their own can be achieved by the system.

Measurements of serial peak expiratory flow (PEF) varies. Many PEF calculations are carried out in connection to symptoms or in early morning and evening. According to one embodiment, the percentage of diurnal variability is based on the following; day's highest minus day's lowest, divided by mean of day's highest and lowest, and weekly variability by averaged diurnal over one week. The variability is positively confirmed if the averaged diurnal or weekly percentage, respectively, for adults; >10% or >20% and children; >13% or >20%, requiring at least twice-daily PEF readings over 2-4 weeks. Although serial measurements assessing variability in PEF has been included in asthma guidelines for decades, clinicians rarely use it due to time consuming calculations reading of paper PEF plots, patients having poor adherence to the measurement and interpretation difficulties. The advantages of monitoring with PEF is the low cost.

According to one embodiment, the system may comprise any of the embodiments disclosed herein and an improved spirometry software to assist performance and interpretation of home digital spirometry, to improve that as well as support interpretation of the same spirometry. The processor (35) in any of the embodiments disclosed herein may be further configured to give one or more indicators, feedback, to the user to change how the spirometer measurement is done, how the inhale or exhale is done, as described above. The computer controlled system may identify common mistakes and errors which occur when performing spirometry in real time. The system (30) may analyse data in real time and instruct the user to help reduce these errors and mistakes by the configuration of the processor (35). In addition, one may observe professional interpretation of spirometry results and develop and evaluate machine learning software, algorithms, that can assist healthcare staff in interpretation. By feeding the system (30) with acceptable spirometry, the processor (35) may be configured to compare the acceptable flow curves of the spirometry with the flow curve of a user, and give indicators, feedback, to the user so that a proper and acceptable spirometry can be made. By using embodiments described above users may measure forced expiratory volume in one second (FEV1). The system may give immediate feedback on the performed measurement so that correct spirometry may be performed.

Further Embodiments

Disclosed is a first embodiment comprising an adapter for a mobile hand-held inhaler, the adapter (70) comprising
a battery (71);
a memory (72);
a processor (77);
a sensor (73) measuring sound and/or vibration;
fastener (74) for attaching the adapter to the mobile hand-held inhaler; and
a transmitter (75) and a receiver (76) for communicating electronically with an external (mobile hand-held) computer (30);
wherein the processor (77) (and/or the adapter (70)) is configured for using the sensor (73) to sense/measure sound and/or vibrations caused by operating the mobile hand-held inhaler (10) to provide lung medication, for storing the sensed sound and/or vibrations as data (78) in the memory (72), and for communicating the stored data (78) to the external (mobile hand-held) computer (30).

Disclosed is a second embodiment comprising the adaptor according to the first embodiment, wherein the processor (77) (adaptor) is further configured for storing the sensed sound and/or vibration data; and configured for communicating the stored data to the external (mobile hand-held) computer when the transmitter and receiver can communicate electronically (is in range) with the external computer.

Disclosed is a third embodiment comprising the adaptor according to the first or second embodiments, wherein the fastening means is adhesive or elastic means (the elastic means may surround the inhaler).

Disclosed is a fourth embodiment comprising the adaptor according to any one of the preceding first to third embodiments, further comprising features of the computer controlled dosage system as mentioned in the tenth embodiment and onwards.

Disclosed is a fifth embodiment comprising a computer controlled dosage system, for dosage adjustment for a mobile, hand held, inhaler (10) for delivering a dosage of a medicine, comprising:
a spirometer (20) for measuring lung function (24);
the adaptor (70) of claim 8, the adaptor being attachable to the mobile, hand-held, inhaler (10);
a handheld mobile computer (30) separate from the inhaler (10), separate from the spirometer (20), and separate from the adaptor (70), the computer (30) being configured to communicate electronically with the spirometer (20) and the adaptor ( ), the computer (30) comprising a processor (35), a screen (38), and a memory (36);
wherein the processor (35) of the computer (30) is configured to receive a manual input (50) for storage in the memory (36) of the computer (30);
wherein the processor (35) of the computer (30) is configured to receive measured lung function data electronically from the spirometer (20), and to store lung function data in the memory (36) of the computer (30);
wherein the processor (35) of the computer (30) is configured to create a data set (32) for setting a plurality of levels of different dosages (321, 322, 323) of medicine based on at least the medicine used by the inhaler (10), and the manual input (50); wherein the processor (35)

of the computer (30) is further configured to store the data set (32) in the memory (36) of the computer (30);

the processor (35) being further configured for analyzing the measured sound and/or vibrations to generate an indication (an adaptor/inhaler use indicator) if the hand-held inhaler has provided lung medication (and then indicate that lung medication has been taken);

wherein the processor (35) is further configured to generate an indication (34) on the screen (38) indicating a dosage adjustment for the inhaler (10), based on the measured lung function (24), the use indicator, and on one of the plurality of levels of dosage (321, 322, 323) of the data set, the indication (34) indicating one of the plurality of levels of dosage (321, 322, 323) of the data set (32) as the dosage adjustment for the inhaler (10).

Disclosed is a sixth embodiment comprising the computer controlled dosage system according to the fifth embodiment, wherein the processor (35) is further configured for improve to analyze the sound and/or vibration data by, in response to the indication (34) to use inhaler dosage adjustment, store the sound and/or vibration occurring during providing the medication of the inhaler; and use the known sound and/or vibration to further improve future analyzation of the sound and/or vibration to generate the use indicator.

Disclosed is a seventh embodiment comprising the computer controlled dosage system according to the fifth embodiment, wherein the processor (35) is further configured for improve to analyze the sound and/or vibration data by receiving the manual input (50) indicating that a user of the system is going to use the inhaler;

store the sound and/or vibration occurring during the use of the inhaler providing the medication; and use the known sound and/or vibration to further improve future analyzation of the sound and/or vibration to generate the use indicator.

Disclosed is a eight embodiment comprising the computer controlled dosage system according to any one of the fifth to seventh embodiments, wherein the adapter stores the measured sound and/or vibration until the handheld mobile computer communicates electronically with the transmitter and receiver of the adaptor to download the stored sound and/or vibration data to the memory of the handheld mobile computer.

Disclosed is a ninth embodiment comprising a computer controlled dosage system, for dosage adjustment for a mobile, hand held, inhaler (10) for delivering a dosage of a medicine, comprising:

a spirometer (20) for measuring lung function (24);

a handheld mobile computer (30) separate from the inhaler (10), separate from the spirometer (20), and comprising the adaptor/sensor, the computer (30) being configured to communicate electronically with the spirometer (20) and the adaptor/sensor, the computer (30) comprising a processor (35), a screen (38), the sensor for measuring sound (of the inhaler providing medication), and a memory (36);

wherein the processor (35) of the computer (30) is configured to receive a manual input (50) for storage in the memory (36) of the computer (30);

wherein the processor (35) of the computer (30) is configured to receive measured lung function data electronically from the spirometer (20), and to store lung function data in the memory (36) of the computer (30);

wherein the processor (35) of the computer (30) is configured to create a data set (32) for setting a plurality of levels of different dosages (321, 322, 323) of medicine based on at least the medicine used by the inhaler (10), and the manual input (50); wherein the processor (35) of the computer (30) is further configured to store the data set (32) in the memory (36) of the computer (30);

the processor (35) being further configured for analyzing the measured sound to generate a use indicator (indicating if the hand-held inhaler has provided lung medication) (and then indicate that lung medication has been taken);

wherein the processor (35) is further configured to generate an indication (34) on the screen (38) indicating a dosage adjustment for the inhaler (10), based on the measured lung function (24), the use indicator, and on one of the plurality of levels of dosage (321, 322, 323) of the data set, the indication (34) indicating one of the plurality of levels of dosage (321, 322, 323) of the data set (32) as the dosage adjustment for the inhaler (10).

Disclosed is a tenth embodiment comprising a computer controlled dosage system, for dosage adjustment for a mobile, hand held, inhaler (10) for delivering a dosage of a medicine, comprising:

at least one measuring device (20) for measuring at least one parameter (24);

a handheld mobile computer (30) separate from the inhaler (10), the computer (30) being configured to communicate with the at least one measuring device (20) and with a remote memory (40) for sending and receiving information (42) to and from patient medical records of the remote memory (40) for storage in a memory (36) of the computer (30), and the computer (30) being configured to receive a manual input (50) for storage in the memory (36) of the computer (30);

wherein the computer (30) is configured to create a data set (32) for setting a plurality of levels of different dosages (321, 322, 323) of medicine based on the medicine used by the inhaler (10), the information (42) from the patient's medical records of the remote memory (40), and the manual input (50);

wherein the computer (30) is further configured to store the data set (32) in the memory (36) of the computer (30);

wherein the computer (30) is further configured to generate an indication (34) indicating a dosage adjustment for the inhaler (10), based on the at least one parameter (24) and on one of the plurality of levels of dosage (321, 322, 323) of the data set, the indication (34) indicating one of the plurality of levels of dosage (321, 322, 323) of the data set (32) as the dosage adjustment for the inhaler (10).

Disclosed is a eleventh embodiment comprising the system according to the tenth embodiment, wherein the computer (30) is further configured to receive an automatic input (60) and the configuration for generating the indication (34) further is based on the automatic input (60).

Disclosed is a twelfth embodiment comprising the system according to the tenth or eleventh embodiments, wherein the indication (34) is a text and/or graphic message on a screen (38) of the computer (30).

Disclosed is a thirteenth embodiment comprising the system according to any one of the preceding twelve embodiments, wherein the measuring device (20) is one or more of the following group: a spirometer, an accelerometer, a pulse oximeter, an impulse oscillometer (IOS), a blood sample device, a flow meter for lungs, a peak flow meter, a device sampling marker of inflammation, and/or a device sampling marker of inflammation from exhaled air.

Disclosed is a fourteenth embodiment comprising the system according to any one of the preceding thirteen embodiments, wherein the indication (34) is a dosage adjustment by one of the following adjustments or by a combination of one or more of the following adjustments:
- adjusting the amount of medicine delivered at each inhalation;
- adjusting the frequency of inhalations;
- adjusting the number of inhalations; and
- adjusting by adding a further medicine.

Disclosed is a fifteenth embodiment comprising the system according to any one of the preceding fourteen embodiments, wherein the computer (30) is a mobile phone and the configuration of the computer (30) is an application on the mobile phone or an application in an internet cloud.

Disclosed is a sixteenth embodiment comprising the system according to the eleventh embodiment, wherein the automatic input (60) is one or more of the following group: pollen levels, air pollution, weather conditions, biological parameter, pollen index, lung volume, air flow to or from lung, blood sample, blood sugar level, body weight, body surface area, environmental condition, humidity, air pressure, height above sea level, GPS position, recent or future user activity, nutrition intake, or user data.

Disclosed is a seventeenth embodiment comprising the system according to any one of the preceding sixteen embodiments, wherein the system further comprises a reminding system to communicate when a dosage should be taken; preferably the communication is made via a phone, a mobile phone, a smartphone, sms, or an e-mail.

Disclosed is a eighteenth embodiment comprising the system according to any one of the preceding seventeen embodiments, wherein the parameter is added manually by the user to the system, and/or the system is configured to collect information and/or parameters from a user's electronic diary, wherein the information from a users's electronic diary comprises past, present, and future information regarding one or more of the following group: gym visits, exercises, and location.

Disclosed is a nineteenth embodiment comprising the system according to any one of the preceding eighteen embodiments, wherein the at least one measuring device (20) is configured to measure markers of inflammation from the airway of a user, preferably a fraction of exhaled Nitric Oxide (FeNO), and the system is configured to use this as the parameter to adjust the dosage of the inhaler.

Disclosed is a twenties embodiment comprising the system according to any one of the preceding nineteen embodiment, wherein the computer is further configured for providing reports or logged information regarding the user's condition based on the at least one measured parameter.

Disclosed is a twenty-first embodiment comprising the system according to any one of the preceding twenty embodiments, wherein the inhaler (10) is configured to provide a dosage of insulin for the treatment of diabetes.

Disclosed is a twenty-second embodiment comprising the system according to any one of the preceding twenty-one embodiments, wherein the inhaler (10) is a powder dose metered inhaler, an aerosol form inhaler, a nebulised form inhaler, or any kind of dosage delivery apparatus.

Disclosed is a twenty-third embodiment comprising the system according to any one of the preceding twenty-two embodiments, wherein the computer (30) is further configured to limit the dosage for the purpose of not adjusting the dosage to a dangerous dosage or to a non-affective dosage, avoiding under- or overmedication.

Disclosed is a twenty-fourth embodiment comprising a dosage regime for a dosage system according to any one of the preceding twenty-three embodiments, wherein a dosage of medicine is adjusted to one of the plurality of levels of dosage (321, 322, 323) of the data set (32).

Any one of these twenty-four embodiments may be combined with any one of the embodiments described by the claims or otherwise mentioned herein.

Further General Description of System

The inhaler (10) may be a purely mechanical inhaler, without any electronic components. The system comprises at least one measuring device (20) for measuring at least one parameter (24). This may for example be a spirometer allowing measurement of lung function and providing such a measurement as a parameter (24) to the system.

The system comprises a handheld mobile computer (30). This may for example be a mobile smart phone. The computer (30) is separate from the inhaler (10). The dosage deliverer (10), inhaler (10), does not comprise a computer. This allows the system to work with any inhaler (10). The computer (30) is configured to communicate with the at least one measuring device (20). The computer (30) is further configured to communicate with a remote memory (40) for sending and receiving information (42) to and from patient medical records of the remote memory (40). This allows for a two way communication between the remote memory (40) and the computer (30). The remote memory (40) is not part of the computer (30) or the inhaler (10) and is, for example, a large central data base comprising patient data. This information (42) may be stored in a memory (36) of the computer (30). The computer (30) is also configured to receive a manual input (50), and this input (50) may be stored in the memory (36) of the computer (30).

The computer (30) is configured to create a data set (32) for setting a plurality of levels of different dosages (321, 322, 323) of medicine. This data set (32) may be a treatment plan according to national requirements or legislation. The configuration of this data set (32) is based on the medicine used by the inhaler (10), the information (42) from the patient's medical records of the remote memory (40), and the manual input (50). This allows the computer to create a data set that comprises a plurality of different levels, e.g. green (321), yellow (322), and red (323), of different dosages of the medicine tailored to a user, but also according to the patient's medical records, the medicine and answers to questions asked by the computer (manual input), and technically fulfilling national requirements or legislation. Thus, the configuration for creating the data set (32) can be a pre-set condition, such as a national standard or regulation. The plurality of levels of different dosages of medicine can be any number, for example, 2, 3, 4, 5, 6, 7, 8, 9, or more. The computer (30) may further be configured to store the data set (32) in the memory (36) of the computer (30).

The computer (30) is further configured to generate an indication (34). This indication (34) is indicating a dosage adjustment for the dosage system, the inhaler (10), based on the at least one parameter (24) and on one of the plurality of levels of dosage (321, 322, 323) of the data set. The indication (34) is indicating one of the pluralities of levels of dosage (321, 322, 323) of the data set (32) as the dosage adjustment for the inhaler (10).

In one embodiment, which may apply to the entire disclosure, the computer (30) may have a processor. The configuring the computer may be done by configuring the processor of the computer (30).

A technical effect of the computer controlled dosage system, as claimed in claim 1, is given by how the different components (20, 30) are arranged and how they are connected, and the way the computer (30) has been configured. This allows the system to technically provide the data set (32) and technically define the different levels of dosage (321, 322, 323). It is this technical configuration of the system that achieves the data set to be generated, not merely defined, and useful for dosage adjustment. Important is that the system is configured to adapt the data set (32) to the national legislation or other predetermined rules, making it technically possible to use the system in real life and integrate the system in the national health care system. Furthermore, the arrangement of the different components (20, 30) of the system, how they are connected, can communicate, and how they are configured, allows the system to provide an indication of the dosage. This indication may be a level of dosage from the data set. This indication may, as an example and in a simple form, be a text message, and allows the dosage system, e.g. an inhaler, to give an adjusted dosage, not too much or too little (overmedicating or undermedicating).

According to one embodiment, the computer (30) may further be configured to receive an automatic input (60) and the configuration for generating the indication (34) may further be based on the automatic input (60). Such an automatic input (60) may be one or more of the following group: pollen levels, air pollution, weather conditions, biological parameter, pollen index, lung volume, air flow to or from lung, blood sample, blood sugar level, body weight, body surface area, environmental condition, humidity, air pressure, height above sea level, GPS position, recent or future user activity, nutrition intake, or user data. The computer may be configured such that the automatic input may be pulled in via the internet or any other accessible remote data.

According to one embodiment, the indication (34) may be a text and/or graphic message on a screen (38) of the computer (30). The computer (32) may indicate, e.g. on a screen or by sound, the adjustment to the dosage and the user may make the adjustment. The indication (34) may be a dosage adjustment by one of the following adjustments or by a combination of one or more of the following adjustments: adjusting the amount of medicine delivered at each inhalation; adjusting the frequency of inhalations; adjusting the number of inhalations; and adjusting by adding a further medicine. For example, a dosage adjustment could be moving from a first level of two inhalations every morning and evening to a second level of three inhalations every morning, midday, and evening. For example, a dosage adjustment can be effected by subsequent actuation of the dosage system, the inhaler. The system may be configured to provide the user of the inhaler with information how to adjust the dosage of the inhaler. For example, the system may inform the user that two inhalations should be taken rather than only one inhalation each time. For example the system may inform the user that six inhalations should be taken within 24 hours, rather than only four inhalations. This would allow a user to take the correct dosage, thus allowing the dosage of the medication to be taken in the most effective way for the user.

According to one embodiment, the measuring device (20) may be one or more of the following group: a spirometer, an accelerometer, a pulse oximeter, an impulse oscillometer (105), a blood sample device, a flow meter for lungs, a peak flow meter, a device sampling marker of inflammation, and/or a device sampling marker of inflammation from exhaled air.

According to one embodiment, the computer (30) is a mobile phone and the configuration of the computer (30) is an application on the mobile phone or an application in an internet cloud. The computer may be a part of a smart phone, tablet, or similar. The configuration of the computer may be the configuration of a processor within the computer. The configuration may be done by an application and by providing any necessary hardware.

According to one embodiment, the system may further comprise a reminding system to communicate when a dosage should be taken; preferably the communication is made via a phone, a mobile phone, a smartphone, sms, or an e-mail. This may ensure that a dosage is actually taken, or at least noted.

According to one embodiment, the parameter (24) is added manually by the user to the system, and/or the system is configured to collect information and/or parameters from a user's electronic diary, wherein the information from a user's electronic diary comprises past, present, and future information regarding one or more of the following group: gym visits, exercises, and location. For example, if a user has been to the gym, entering that into a dairy, or manually directly into the system, the system may be configured to take account of that information when generating the indication for dosage adjustment.

According to one embodiment, the at least one measuring device (20) may be configured to measure markers of inflammation from the airway of a user, preferably a fraction of exhaled Nitric Oxide (FeNO). Additionally, the system may be configured to use this as the parameter to adjust the dosage indication for the inhaler.

According to one embodiment, the computer may further be configured for providing reports or logged information regarding the user's condition based on the at least one measured parameter (24). This report may be displayed on the computer itself (on the screen (38)), and/or may be sent to the remote memory (40) for access by others, e.g. medical staff. This may allow for the system to be supervised according to national legislation. As a result, information may be sent back to the system, allowing a modification/improvement of the dosage system, e.g. by generating a modified data set (32) allowing for improved dosage adjustment.

According to one embodiment, the dosage delivery system, the inhaler (10), may be configured to provide a dosage of insulin for the treatment of diabetes. As such, the system may be suitable for any kind of medicine. According to one embodiment, the inhaler (10) may be a powder dose metered inhaler, an aerosol form inhaler, a nebulised form inhaler, or any kind of dosage delivery apparatus.

According to one embodiment, the computer (30) may be further configured to limit the dosage for the purpose of not adjusting the dosage to a dangerous dosage or to a non-affective dosage, avoiding under- or overmedication. This may depend on the medicine used and the medicine used may be input to the system as a manual input, thus the computer may be configured to receive a manual input of what medicine is used.

According to one embodiment, a dosage regime is disclosed for a dosage system as described herein with reference to any one embodiment or combination thereof, wherein a dosage of medicine is adjusted to one of the plurality of levels of dosage (321, 322, 323) of the data set (32). The system generates the data set (32) that comprises a plurality of levels of different dosages (321, 322, 323). The dosage regime comprises the system indicating what level of dosage should be taken by a user. As disclosed and explained herein, the system generates a dosage regime for the user and the medicine in question. In this way the dosage of the medicine may be given to a user resulting in the most effective dosage given, and avoiding giving a dangerous dosage or a non-affective dosage.

According to embodiments, the system may be configured to limit the dosage for the purpose of not adjusting the dosage to a dangerous dosage or to a non-affective dosage. This may be done to comply with health regulations and/or any attempted misuse of the inhaler (10).

According to at least one embodiment, the indication (34) may be no adjustment at all, thus maintaining the present dosage. This would indicate that the dosage used is the appropriate and effective dosage.

In one embodiment, the at least one measuring device (20) is configured to measure markers of inflammation from the airway of a user, preferably a fraction of exhaled Nitric Oxide (FeNO), and the system is configured to use this as the parameter to adjust the dosage of the inhaler.

At least one of the embodiments provides a computer controlled inhaler system with the objective to administer pharmaceutical compounds. It can contain medicine in powder form (powder dose metered inhaler), aerosol form, or nebulised form. The dose can be adjusted, allowing the dose of inhaled medicine to be increased or reduced, tailored, to that specific user's requirements. The dose adjustment function allows for optimisation of treatment by increasing or reducing the dose without delay when required. This also reduces the total amount of medicine administered. The system may comprise the administering device (powder dose metered inhaler, aerosol form or nebulised form) and may be used for all medical conditions where inhaled medicine is appropriate.

A dosage may be the amount of medicine given, the administration of medicine in doses, and/or the number or frequency of doses. Dosage may be the administration of a drug or agent in prescribed amounts and at prescribed intervals. Dosage may be the optimum therapeutic dose and optimum interval between doses. The dose may be electronically controlled via software that adjusts the administered dose depending on the at least one parameter. It may take a range of other factors into account when calculating the dose.

According to at least one embodiment, a computer controlled dosage system could also be used with conventional inhalers informing the user how many inhalations to take any day. An example of use is for users with asthma or chronic obstructive pulmonary disease (COPD), diseases that are characterised by variability where the dose may need rapid adjustment upwards or downwards. Another compound that may be administered via inhalation is insulin for the treatment of diabetes. For example, a dosage for diabetes may be adjusted each time taken. Embodiments of the system software may have other uses such as for example: communicate with the patient's treating doctor or nurse to inform him/her of any exacerbation in the patient's condition; collect information from the internet or relevant institutions regarding environmental conditions such as weather, humidity, smog/fine particle levels, pollen levels and take these into account when calculating the dose. This information can be related to the user's geographical location as identified by gps or smartphone location as there may be local variations regarding proximity to heavy traffic or going to the countryside where pollen levels may be higher.

According to at least one embodiment, a user may make manual adjustments either by entering information by hand or letting the device collect information from the user's electronic diary about gym visits and/or exercise where the dosage may need adjustment.

According to at least one embodiment, the system may collect information from other devices measuring markers of disease. These devices can be anything from taking simple home blood tests to devices that measure markers of inflammation from the airway such as for example the fraction of exhaled Nitric Oxide (FeNO). The latter is useful for patients with allergic asthma. The collected information, parameters, may be used to adjust the dosage.

According to at least one embodiment, the system may provide reports or logged information for the benefit of treating medical staff or the user him or herself regarding the user's condition as well as compliance to medication.

According to at least one embodiment, the system may link with the user's medical records giving treating medical staff information about the user's condition and making dosage adjustments improving treatment.

Turning to some more specific embodiments, the computer controlled system overcomes one or more problems mentioned above by supporting self-management of the disease, improving communication between user and healthcare as well as making health care more efficient while also increasing the quality of clinical decisions. The system may be an easy-to-use self-management application with portable spirometry to enable healthcare to better follow guidelines without increasing number of visits while also reducing number of unplanned visits given that dosage can be adapted to variable factors over time (lung function, health condition, weather, pollen count etc.) and given that users' motivation to follow the dosage will increase. The user may take control over the disease and experience an increase in quality of life.

At least one embodiment may benefit asthma/COPD patients and care providers as well as specialized lung clinics. The may provide more timely and accurate diagnosis; more efficient organization of the clinical work; more focus on structured patient evaluation; increased capacity and competence of health care professionals, particular general practitioners; and improved user education and self-management programs.

At least one embodiment of the system may provide a user the possibility of self-monitoring and to achieve disease control. The user will get dosage recommendations based on variable factors without spending much time with the application. The dosage system, for example for asthma and COPD, may be arranged in relatively clear guidelines by international consensus. Specifically there are steps wherein the gathered information on symptoms, lung function, etc. may be transferred into information on dosage (e.g. frequency) of medication. The system will let a user or health care worker know clearly which dosage step they should be following and thereby improve individualized care. Tailored dosage leads to reduced risk of side effects. The system may also educate users in self-management and for example remind asthma patients to take the allergy medication when the pollen count of their specific allergy goes up. Potentially, the end result will be an empowered and motivated user achieving increased quality of life. The improved communication possibility benefits both healthcare and users. Healthcare can decide what information they want to collect from the system and how frequently. The most fundamental biological end marker that may be collected regularly is one or two lung function parameters. Seeing longitudinal changes of lung function may improve the quality of decisions made and in addition has valuable diagnostic and prognostic information. The user will be able to easily access an updated individual dosage plan if needed without visiting the primary care facility saving time and money for all involved.

According to one specific exemplary embodiment, the system may comprise a small lung function measurement device (a spirometer). The cost of this is comparable to very simple peak flow meters for home use. The spirometer can be used with a smartphone that will be configured by an application. The data collected by the system may be visible in the patient's medical records of the remote memory. The remote memory may be direct, or indirectly, via an internet based portal to the national health care. By doing this, information such as, for example, asthma or COPD, known allergies, medications, weight, and height will be entered into the app which can then establish a treatment plan according to national and international guidelines for every patient. The user will be able to measure their lung function themselves and will receive questions. This information collected by the system, together with information on for example pollen counts, air pollution and influenza epidemics, will generate an indication of the dosage. The system may send data to the health care provider so that for example lung function over time can be displayed in the medical record at the next visit at the health care provider. The possibility of contacting the health care system can also be used to automate procedures like booking appointments, requesting new prescriptions or similar.

According to one exemplary embodiment, the system may comprise a smart phone, a computer, configured to receive manual data input (for example, age, sex, anthropometrics, comorbidities, informed consent, answer burden symptoms and intake of dosage, schedule reminders for intake of dosage, dosage adherence, set alerts according to information gathered in automatic data input); automatic data input (for example: pollen levels, air pollution, weather conditions, GPS location, data from additional devices); data from additional devices (for example, connected via Bluetooth, spirometer, accelerometer, registrations of sleep and physical activity); and hands-on guidance through national service portal to a remote memory (for example, inquiry to physician, prescription, dosage adjustment, schedule clinical visits, transfer individual information of e.g. symptoms and lung function). The computer may display graphs and statistics, and visual a dosage plan.

According to one embodiment, the computer is configured to comprise three modules: Manual Data Input, Automatic Data Input and Hands-on guidance, as described above. The module Manual data input may include personal data and personalized settings for each user. In addition, the system may ask users, at regular intervals (from daily to monthly basis) to register symptoms through validated questionnaires. In Automatic data input user-generated data may be gathered from the portable spirometer together with relevant background information from external web services. Web services may provide air quality information of pollen levels, weather conditions and particle concentrations based on GPS-location or other selected location. In Manual data input, optional alerts are set in relation to poor air quality. In case of severe conditions, the system may recommend an alert to be send to a clinic through secure access of Hands-on guidance.

According to one embodiment, hands-on guidance may provide a user with information and self-management support through any national portal to any national health care system. Such service may allow for a two-way communication between user and health care professionals. Examples on how hands-on guidance may be used: automatic transfer of user's dosage plan from the primary source (medical record) to the system. This may be a treatment plan following national plans and regulations, provided by a national board of health and welfare; follow a user's medical adherence (e.g. based on manual data input); the possibility to set clinical alerts in case of impairment (symptoms, lung function, environmental factors or increased need of medication alerts signs of exacerbations); the possibility of contacting health care provider through inquiries; and transfer gathered information of biological end markers from the system for clinical evaluation.

According to one embodiment, the system may be configured for measurement of lung function in a more detailed way, and for giving the user immediate visual feedback and dosage adjustment recommendations. It may also be configured to provide a possibility of transferring information to a user's health care provider. The system may help to automate a dosage plan so that more users can have their individual dosage plans according to recommendations and, in addition, as it is provided electronically in their mobile phone, will carry it with them wherever they may need it.

According to at least one embodiment, the success of a user's self-management is depended on dedicated healthcare providers or a key individual who work closely with the treating physician. In other words, users should not be left alone, and self-management is not a goal itself that replace proactive involvement from health care professionals. The claimed system may enable evaluation of user's symptoms, lung function, intake daily medication automatic data input of user dosage plan, air quality based on particle concentrations, pollen and weather conditions. The concept also enables users to send inquiry to the clinic, schedule appointments and transfer gathered information to a clinic for hands-on guidance. Furthermore, the system may provide choice of medication and dosage adjustments. The system may reduce a burden of disease for individuals and society, reduction of emergency visits.

According to at least one embodiment, the system overcomes one or more of the problems mentioned above by supporting self-management of a disease, improving communication between patient and healthcare as well as making health care more efficient while also increasing the quality of clinical decisions. An easy-to-use self-management application with portable spirometry will enable healthcare to better follow guidelines without increasing number of visits while also reducing number of unplanned visits given that a user's dosage plan can be adapted to variable factors over time (lung function, health condition, weather, pollen count etc.) and given that a user's motivation to follow treatment will increase.

It will be apparent to those skilled in the art that various modifications and variations can be made to the system and dosage regime. Especially that one or more of the embodiments disclosed above can be combined with each other to achieve the overall goals with the system. Other embodiments will be apparent to those skilled in the art from consideration of the specification and practice of the disclosed system and dosage regime. It is intended that the specification and examples be considered as exemplary only, with a true scope being indicated by the following claims and their equivalents.

The invention claimed is:

1. A system for collecting lung function data, the system comprising:
- a mobile hand-held spirometer for measuring lung function of a user and providing lung function data corresponding to the user's measured lung function; and
- a mobile hand-held computer comprising a processor, a memory, a clock, and a screen;
- wherein the spirometer and the mobile hand-held computer are separate devices, the spirometer and the mobile hand-held computer configured to communicate electronically with each other;
- wherein the processor is configured for
  - collecting the measured lung function data from the spirometer via the electronic communication between the spirometer and the mobile hand-held computer, and
  - storing the lung function data in the memory;
- wherein the processor is further configured for
  - initiating collection, with the system, of lung function data from the user via the spirometer by indicating on the screen of, and/or by a sound from, the mobile hand-held computer for the user to use the spirometer when A) or B) occur, A) and B) comprising:
    - A) when the clock reaches a first predetermined recurring time within successively recurring periods of 24 hours each, with at least 10 hours between the first predetermined recurring time and a second time for collection within the same recurring 24 hour period, and
    - B) before and after the mobile hand-held computer indicates for the user to take any lung medication, or after the mobile hand-held computer indicates that any lung medication has been taken by the user;
  - calculating, by the processor, a variation between all collected lung function data stored in the memory, the variation is the coefficient of variation expressed in percentage;
  - repeating the indication for the user to use the spirometer only when A) or B) occur and repeating the calculation of the variation; and
  - stopping the system to collect measurements from the spirometer or indicating on the screen for the user to stop using the spirometer, when the processor compares the variation between all collected lung function data and determines the variation is more than 20 percent or after a maximum of collecting lung function data for 14 days.

2. The system of claim 1, further comprising:
- a heart rate monitor for measuring the heart rate of the user and providing heart rate data corresponding to the user's measured heart rate, the heart rate monitor being a separate device from the spirometer and the mobile hand-held computer, and the heart rate monitor and the mobile hand-held computer being configured to communicate electronically with each other;
- wherein the processor is further configured for
  - collecting the measured heart rate data from the heart rate monitor via the electronic communication between the heart rate monitor and the mobile hand-held computer, and
  - storing the heart rate data in the memory;
- wherein the initiating collection of lung function data from the user via the spirometer by indicating on the screen of, and/or by a sound from, the mobile hand-held computer when to use the spirometer when A) or B) occur, further comprises C), wherein C) is when the heart rate monitor measures a heart rate for the user of 85 percent, or more, of a predetermined maximum value of the user's heart rate.

3. The system of claim 2, wherein the heart rate measurement in C) has a time period duration of 5 to 10 minutes; and the processor is further configured to subsequently initiate collection of lung function data from the user via the spirometer 5, 10, 15, and 30 minutes after the time period for the heart rate measurement has ended.

4. The system of claim 1, further comprising:
- a hand-held inhaler for providing lung medication for the user; and
- a sensor for measuring sound and/or vibration, the sensor being attached to the hand-held inhaler and the sensor measuring sound generated by operating the inhaler and/or the sound generated by air flow through the inhaler when the user is inhaling, and/or vibrations caused by the user operating the hand-held inhaler to provide lung medication for the user;
- wherein the sensor and the mobile hand-held computer are configured to communicate electronically with each other;
- wherein the processor is further configured for analyzing the measured sound and/or vibrations to determine if the hand-held inhaler has provided lung medication to the user and then to indicate that lung medication has been taken in B) and to initiate collection of lung function data from the user via the spirometer.

5. The system of claim 4, wherein the processor is further configured to analyze the measured sound to determine an inhalation sound and a duration of the sound of the inhalation through the inhaler.

6. The system of claim 1, further comprising:
- a hand-held inhaler for providing lung medication for the user; and
- a sensor for measuring sound, the sensor being integrated in the mobile hand-held computer and the sensor measuring sound caused by the user operating the hand-held inhaler to provide lung medication for the user;
- wherein the processor is further configured for analyzing the measured sound to determine if the hand-held inhaler has provided lung medication to the user and then to indicate that lung medication has been taken in B) and to initiate collection of lung function data from the user via the spirometer.

7. The system of claim 1, further comprising a GPS, wherein the processor is further configured for retrieving the location of the mobile hand-held computer;
- wherein the initiating collection of lung function data from the user via the spirometer by indicating on the screen of, and/or by a sound from, the mobile hand-held computer to use the spirometer when A) or B) occur further comprises D), wherein D) is when the processor determines, by using the GPS, that the mobile hand-held computer is located within a predetermined area, or moves with a predetermined speed for a predetermined duration.

* * * * *